(12) United States Patent
Bauer et al.

(10) Patent No.: US 9,150,814 B2
(45) Date of Patent: Oct. 6, 2015

(54) FILTER APPARATUS

(75) Inventors: Martin Bauer, Lebach (DE); Andreas Schunk, Waldmohr (DE); John Kazimierz Duchowski, Saarbrücken (DE)

(73) Assignee: Hydac Filter Systems GmbH, Sulzbach/Saar (DE)

( * ) Notice: Subject to any disclaimer, the term of this patent is extended or adjusted under 35 U.S.C. 154(b) by 399 days.

(21) Appl. No.: 13/261,150

(22) PCT Filed: May 21, 2010

(86) PCT No.: PCT/EP2010/003145
§ 371 (c)(1),
(2), (4) Date: Jan. 24, 2012

(87) PCT Pub. No.: WO2011/012184
PCT Pub. Date: Feb. 3, 2011

(65) Prior Publication Data
US 2012/0118809 A1    May 17, 2012

(30) Foreign Application Priority Data

Jul. 30, 2009  (DE) .......................... 10 2009 035 401

(51) Int. Cl.
| | | |
|---|---|---|
| *B01D 29/11* | (2006.01) | |
| *B01D 29/56* | (2006.01) | |
| *B01D 29/58* | (2006.01) | |
| *C10M 175/00* | (2006.01) | |
| *C07F 9/02* | (2006.01) | |
| *B01J 47/04* | (2006.01) | |
| *B01D 27/14* | (2006.01) | |

(Continued)

(52) U.S. Cl.
CPC ......... *C10M 175/0058* (2013.01); *B01D 29/11* (2013.01); *B01J 47/04* (2013.01); *C07F 9/025* (2013.01); *B01D 24/12* (2013.01); *B01D 27/02* (2013.01); *B01D 27/148* (2013.01); *B01D 35/0276* (2013.01); *B01J 47/022* (2013.01); *B01J 47/024* (2013.01); *C10M 2203/1006* (2013.01); *C10M 2207/023* (2013.01); *C10M 2223/04* (2013.01)

(58) Field of Classification Search
CPC ........ B01D 29/56; B01D 29/58; B01D 24/12; B01D 27/02; B01D 27/148; B01D 35/0276; C07F 9/025; C10M 175/0058; C10M 2203/1006; C10M 2223/04; C10M 2207/023; B01J 47/022; B01J 47/04; B01J 47/024
USPC ............. 210/167.04, 172.2, 172.3, 266, 282, 210/287, 289, 448, 502.1, 683, 686, 690; 554/191
See application file for complete search history.

(56) References Cited

U.S. PATENT DOCUMENTS 2,668,622 A * 2/1954 Irvine et al. .................... 210/186
2,736,698 A * 2/1956 Klumb et al. ................... 521/26
(Continued)

FOREIGN PATENT DOCUMENTS

| EP | 0 696 311 | 12/2001 |
|---|---|---|
| GB | 2 142 939 | 1/1985 |

(Continued)

*Primary Examiner* — Matthew O Savage
(74) *Attorney, Agent, or Firm* — Roylance, Abrams, Berdo and Goodman LLP

(57) ABSTRACT

A filter apparatus (10) for cleaning functional fluids, especially selected from phosphate esters, phosphate ester-based oils, mineral oils and phenols, includes a filter housing (12) into which a filter bed (14) has been introduced. The filter bed has a mixture of anionic and cationic ion exchange resins. At least one filter element (16), designed as a flow guide device, enables the diversion of the fluid from a radial to an axial flow direction (18) or vice versa.

31 Claims, 1 Drawing Sheet

(51) Int. Cl.
*B01D 27/02* (2006.01)
*B01J 47/02* (2006.01)
*B01D 35/027* (2006.01)
*B01D 24/12* (2006.01)

(56) References Cited

U.S. PATENT DOCUMENTS 3,174,623 A * 3/1965 Sloan ............................ 210/285
3,954,624 A * 5/1976 Petrucci ....................... 210/439
4,741,857 A    5/1988 Horwitz et al.
5,545,319 A * 8/1996 Hart et al. ..................... 210/279
5,661,117 A * 8/1997 Dufresne ...................... 508/433
7,172,694 B2   2/2007 Bortnik
2009/0001023 A1* 1/2009 Dufresne et al. ............. 210/692

FOREIGN PATENT DOCUMENTS

WO    WO 00/58222    10/2000
WO    WO 01/07090     2/2001

* cited by examiner

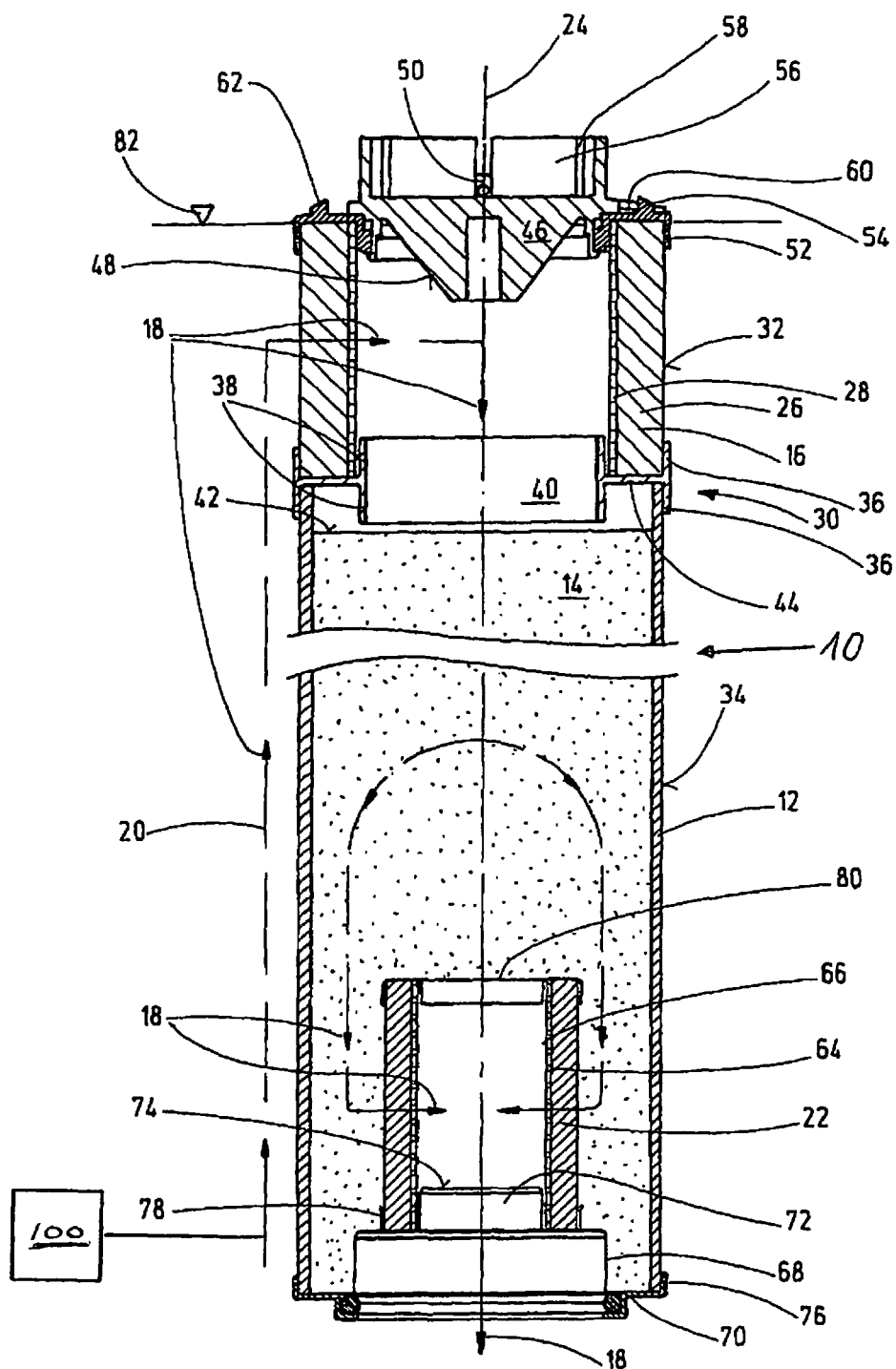

FILTER APPARATUS

FIELD OF THE INVENTION

The invention relates to a filter apparatus for cleaning of functional fluids, especially chosen from among phosphate esters, phosphate-ester based oils, mineral oils, and phenols, having a filter housing into which a filter bed is inserted. The filter bed especially has a mixture of anionic and cationic ion-exchange resins.

BACKGROUND OF THE INVENTION

These functional fluids are used in hydraulic systems, such as, for example, gas turbines and steam turbines, and in the turbine control as lubricants or also as hydraulic media. Often, in addition to needing to be suitable as lubricant media or hydraulic media, the fluids must be poorly flammable. To achieve proper operation of the respective hydraulic system, the fluid used, during the entire time that it circulates, for example, in a fluid circuit of the hydraulic system, must have a very high quality. In particular, impurities of any kind that accompany especially the degeneration of the fluid in use are to be allowed only up to a maximum amount, which amount must generally be set very low. Therefore, in hydraulic systems that do not provide cleaning of the fluid, when a maximum allowable contamination is reached, the complete replacement of the used fluid by a new fluid is necessary. This replacement is, on the one hand, very labor-intensive in most hydraulic systems, and, on the other hand, the indicated fluids are very expensive, especially when they are endowed with special properties such as being poorly flammable and the like. This disadvantage of replacement prompts a legitimate interest in prolonging the service life of the fluid used. The cleaning of the fluid in particular lends itself for accomplishing this purpose.

Filter apparatus having a filter bed of anionic and cationic ion-exchange resins (U.S. Pat. Nos. 3,708,508 and 4,741,857) are used to remove corrosive acids from functional fluids, especially poorly flammable, phosphate ester-based hydraulic fluids (HFD-R). Aging of these fluids is due to hydrolysis, in which the decomposition products are, for instance, corrosive fluids. The neutralization number $N_z$, in English also referred to as "TAN" (Total Acid Number), and the content of metal soaps can be reduced by special ion-exchange resins. In addition to this cleaning of the fluids, continuous dewatering of the fluid is often carried out as well. The desired value of the neutralization number of the cleaned fluid is $N_z \leq 0.1$ mg $KOH/g_{fluid}$. For practical use of the fluids in hydraulic systems, values of the neutralization number $N_z$ of up to 1 mg KOH per gram of fluid can be easily achieved.

EP 0 696 311 B1 discloses a method for treatment of a nonaqueous functional fluid, selected from among phosphate esters, mineral oils, and carboxylate esters, in which a portion of the fluid quantity makes contact with an anionic ion-exchange resin in the presence of enough water so that the acid content of the fluid can be reduced. Then, in the known solution, the removal of water from the fluid by vacuum dewatering and finally the combination of the treated fluid with the bulk of the remaining fluid take place (in situ).

U.S. Pat. No. 5,661,117 B1 discloses a method for regeneration of phosphate ester lubricating fluids in which the lubricating fluid circulates in a mechanical system and is contaminated with metallic material and phosphorus-based acids. Cleaning leads to a new fluid quality with a TAN (Total Acid Number) of 0.03. The method includes essentially the following steps:

Preparation of a source of a phosphate ester lubricant that circulates in a mechanical apparatus and that has at least one metal from the group consisting of aluminum, chromium, tin, iron, sodium, calcium, magnesium and silicon, and has phosphorus-based acids;

Preparation of a source of anionic ion-exchange resin in a cartridge in fluid communication with the apparatus, with the resin having a liquid content of at least roughly 50%;

Introduction of the phosphate ester lubricating fluid contaminated with the metals and the acids for purposes of contact with the resin; and Removal of the metallic compounds and the acids, using the resin by replacing the filter with a periodicity of up to 27 months, when there is a rise in the TAN of roughly 0.07 to make available a reusable lubricating fluid that is essentially free of impurities in new quality and that has a Total Acid Number of 0.03.

SUMMARY OF THE INVENTION

An object of the invention is to provide an improved filter apparatus for cleaning of functional fluids, that, in addition to a compact structure, ensures high reliability and simple manageability in practical use. The cleaning of the functional fluid in the filter apparatus according to the invention is intended to lead to a high-quality fluid with the best possible use being made of the filter bed. Furthermore, the filter apparatus is also to be able to be easily retrofitted into existing hydraulic systems.

This object is basically achieved according to the invention by a filter apparatus connected in the bypass flow to an existing tank of a hydraulic system. An exactly matched fluid volumetric flow passes through a filter bed of preferably anionic and cationic ion-exchange resin in transverse flow velocity. During this flow, the acids, metallic soaps, and other basic media contained in the fluid and particulate dirt that may be present are removed. In this way, an improvement of the quality of the functional fluid is achieved, for instance, by the lowering of the neutralization number.

In that in the filter apparatus, in addition to one filter bed, at least one filter element designed as a flow guide device allows a diversion of the fluid from a radial into an axial flow direction or vice versa, and a compact unit is formed. In that at least one filter element, designed as a flow guide device, diverts the flow direction of the fluid, the respective structural conditions of the hydraulic system to which the filter apparatus is to be connected can be taken into account to implement the fluid flow directions that are best for optimum cleaning success in this way. For example, a large region around the filter apparatus can be included for particle removal by a radial incident flow on the filter apparatus, while, for example, an axial outflow of the fluid from the filter apparatus is advantageous for connecting pipes or a pump for low-cavitation relaying of the fluid. The solution according to the invention can be executed with a housing made in one piece. Alternatively, a multi-part structure of the filter apparatus in which one or more filter elements are detachably fixed on the rest of the apparatus housing can be provided.

Advantageously, viewed in the flow direction of the fluid, at least one flow guide device can be made as a filter element located upstream of the filter bed, can thus undertake a first particle removal from the fluid especially in the manner of a prefilter and can protect an ion-exchange resin introduced as a filter bed against the ingress of a portion of the contaminants of the fluid. Viewed in the flow direction of the fluid and especially preferred, another flow guide device can be made as a filter element downstream of the filter bed that, in the manner of a protective filter, is used for the re-cleaning of the fluid and the protection of the hydraulic system against possible discharge of the ion-exchange resin. In particular, combining the prefilter upstream of the filter bed and the protective filter downstream of the filter bed into one filter apparatus leads to a very compact structure. The filter apparatus according to the invention is made in the manner of a manageable cartridge that can also be easily retrofitted into existing hydraulic systems within the framework of a retrofit.

Advantageously, one filter element can be seated on one face-side end of the filter housing by a holding device. The outer side of the filter element can form an extension of the outer side of the filter housing. If this holding device allows detachment of one filter element from the filter housing, cleaning one filter element detached from the filter apparatus or replacing one filter element with a new one becomes easily possible. Here, a detachable holding device can be a ring that has been inserted as an adapter between one filter element and the filter housing and that on its outer circumference has peripherally a retaining strip that in the installed state extends both in the direction of one filter element and in the direction of the filter housing. The holding device peripherally encompasses the end region of the filter housing facing the ring. The end region of one filter element facing the ring allows holding one filter element that has been placed on the face-side end of the filter housing. In this way, the ion-exchange resin inserted into the filter housing can be easily changed in which one filter element is separated from the filter housing via the holding device. In this way, ion-exchange resin can be removed from the filter housing or can be reinserted into it.

The further filter element located on the other face side of the filter housing can project into the filter housing. The filter bed can encompass the further filter element so that at a high packing density the filter bed can be accommodated in the filter housing in a space-saving manner.

In that the filter fineness of the further filter element is finer than the particle size in the mixture of the ion-exchange resins, unwanted discharge of the ion-exchange resins from the filter apparatus is avoided so that the cleaned fluid leaving the filter apparatus is not contaminated by particles of the ion-exchange resin. In that the filter bed at least partially encompasses the further filter element as shown, a large-area, low-impediment incident flow of the fluid that has passed through the filter bed against the further filter element is enabled for removing the last particulate dirt by the further filter element designed as fine filter before the fluid leaves the filter apparatus.

Also advantageously, the further filter element can be supported by a base part with its foot part made as an end cap for the filter housing and arranged with its head part coaxially to the longitudinal axis of the filter housing. It can have another passage opening for the exit of the fluid that has been altogether cleaned by the filter apparatus. In that the further filter element is supported by a type of end cap of the filter housing, mounting and optionally replacement of the further filter element of the filter apparatus are simple even in this end region.

Preferably, on its end opposite the base part, the further filter element can be sealed with an end cap on which parts of the filter element can be supported in the manner of a column. Preferably, the diameter of a first column supported by the end cap of the further filter element can be smaller than the passage opening of the holding device, and another column can be arranged concentrically to the first column and supported on the base part of the filter housing to stabilize the first column. If the columns have a different density for the ion-exchange resin of the filter bed, both the trickle speed and the trickle flow characteristic within the filter bed can be set. Thus, for example, the other column, located outermost and made as a hollow column, can support in the compressed frame the solidly made column of lower density that is innermost and can induce an intensified flow characteristic in the direction of the center of the filter apparatus. In the opposite case, the possibility exists of routing fluid medium out of the center to the outer side of the device in order in this way, in spite of the central fluid feed via the upper filter apparatus, to force a uniform fluid penetration of the filter bed. The different columns can also be filled with different contents (percent by amount or volume) of anionic and cationic ion-exchange resins to optimize the process control for filter bed cleaning. In addition to two columns arranged concentrically to one another, several columns can be arranged concentrically within the filter apparatus in the manner of a "column guide."

The active volumes of two columns can be used preferably for fluid cleaning and can be essentially of the same size. The filter bed, viewed in the installed state of the filter apparatus, can be designed to form above the further filter element a closed cylindrical function block in order in turn to achieve centered fluid guidance within the device with a relatively long residence time of the fluid.

The filter apparatus can be advantageously connected in the bypass flow of a hydraulic system and is located below the fluid level of the hydraulic system to prevent air from accumulating in the fluid. By placing the filter apparatus in the bypass flow of the hydraulic system, a matched volumetric flow velocity and traverse flow velocity of the fluid through the filter apparatus can be adjusted so that it can be operated at its optimum operating points. An accumulation of air in the fluid should be avoided, however, so that the filter apparatus should accordingly be located below the fluid level of the hydraulic system. At the same time, however, the attempt is also generally made to keep the height difference between the filter apparatus and the fluid level as small as possible to effectively prevent the inflow of contaminants that are found with greater frequency in the vicinity of the bottom of the tank, intended for the fluid, into one filter element of the filter apparatus.

The anionic ion-exchange resin and the cationic ion-exchange resin, each being present in the form of a granulate, can be advantageously mixed with one another, to form the filter bed. The filter bed can include 60% to 95% anionic ion-exchange resin and 40% to 5% cationic ion-exchange resin, preferably 70% to 90% anionic ion-exchange resin, and 30% to 10% cationic ion-exchange resin. Especially preferred, the ion-exchange resin can be 90% anionic ion-exchange resin and 10% cationic ion-exchange resin.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawings which form a part of this disclosure:

FIG. 1 is a side elevational view in section of one exemplary embodiment of the filter apparatus according to the invention.

DETAILED DESCRIPTION OF THE INVENTION

The FIGURE shows a longitudinal section of one exemplary embodiment of a filter apparatus 10 according to the invention for cleaning of functional fluids. The filter apparatus includes a filter housing 12 in which a filter bed 14 is placed, which filter bed preferably has a mixture of anionic and cationic ion-exchange resins. Furthermore, the filter apparatus 10 has a filter element 16 that, designed as a flow guide device, allows a diversion of the fluid from a radial into an axial flow direction 18. The respective flow direction 18 is shown in FIG. 1 by an arrow oriented accordingly along the approximate fluid flow path 20 shown by a broken line outside and inside the filter apparatus.

Viewed in the flow direction 18 of the fluid, one or a first filter element 16 is located in front of the filter bed 14, i.e., upstream of the filter bed 14, while another flow guide device, made as a second filter element 22, is located following the filter bed 14, i.e., downstream of the filter bed 14.

The filter housing 12 is made as a cylinder with a circular base area, has a longitudinal axis 24 is made preferably of a metallic material or of plastic and is made as a pipe body. The housing hollow interior makes available a receiving space for the added ion-exchange resins 14.

First filter element 16 is made in the form of a circular cylinder and is exposed to incident flow by the fluid from outside the filter apparatus 10 in a radial flow direction 18. On the first filter element outer jacket facing the fluid, a peripheral filter mat 26 is present preferably in pleated form and surrounds a hollow space. On its inner side, the filter mat 26 is supported by a support pipe 28 through which the fluid can penetrate into the interior of filter element 16. The support pipe 28 has roughly the same longitudinal extension in the direction of the longitudinal axis 24 as the filter mat 26 to provide one planar contact surface on each of the two axial face sides or ends of filter element 16. The support pipe 28 is, for example, of a metallic material or a suitable plastic material. The flow path 20 of the fluid pre-cleaned by filter element 16 continues parallel to the longitudinal axis 24 when leaving filter element 16 in the axial flow direction 18 in which the fluid travels to the filter bed 14 when the filter apparatus 10 is being used.

Filter element 16 is seated on the face-side axial end of the filter housing 12, that is the upper end as viewed in FIG. 1, by a holding device 30. The outer side 32 of filter element 16 forms an extension of the outer side 34 of the filter housing 12. The holding device 30 is made in the form of an annular adapter that has a roughly H-shaped cross-sectional profile and is aligned coaxially to the longitudinal axis 24. Looking at the installation position of the filter apparatus 10 shown in FIG. 1, the holding device 30 is located above the filter bed 14 and the filter housing 12. In that the outer side 32 of filter element 16 and the outer side 34 of the filter housing 12 are flush with one another, a flat contact of the radially outer leg 36 of the H-shaped profile of the holding device 30 is ensured both with the outer side 34 of the filter housing 12 and with the outer side 32 of the filter element 16. The upper, radially inner leg 38 of the H-shaped profile of the holding device 30, as viewed in FIG. 1, projects up into the interior of filter element 16 and can optionally be moved into contact with the inner side of the support pipe 28. The other inner leg 38 projects down into the interior of the filter housing 12.

The cavity encompassed by the inner legs 38 of the H-shaped profile of the holding device 30 forms a passage opening 40 for the fluid from which particulate dirt has been removed by filter element 16. The opening 40 is located coaxially to the longitudinal axis 24 of the filter housing 12. In this case, the inner legs 38 of the holding device 30 are located above the level 42 of the inserted filter bed 14. Preferably, a cement bond connects the holding device 30 to the filter housing 12 and filter element 16, but exemplary embodiments are also possible that implement a connection that can be detachably fixed, for example, in the form of a screw union or a clamp connection. A cement bond can be provided as a cement layer applied between the upper face-side end of the filter housing 12 and a web 44 as well as the outer leg 36 of the H-shaped profile of the holding device 30, which leg is the lower one viewed in the direction of FIG. 1. The outer side 34 of the filter housing 12 can be cemented to the filter housing 12 both flush against the web 44 and, along its outer periphery, flat with the lower outer leg 36 of the holding device 30. Filter element 16 can be connected to the holding device 30 by the cement material applied in a peripheral receiving space of the holding device 30, which space extends above the web 44 of the H-shaped profile and is bordered by an outer leg 36 and an inner leg 38.

On its end opposite the holding device 30, filter element 16 and thus the filter apparatus 10 are terminated by an upper end cap 46 made as a flow guide device. A flow guide device part projects into filter element 16, has an essentially trapezoidal cross section and is made with a peripheral sloped surface 48. Filter element 16 is connected to the upper end cap 46 by an adapter ring 54. Adapter ring 54 has a roughly U-shaped cross-sectional form that is opened downward in FIG. 1 and that holds and receives an upper section of filter element 16. In this case, an outer ring 52 formed by the radially outside leg of the U-shaped cross section comes into contact with the outer side 32 of filter element 16. The radially inner leg of the U-shaped profile is moved into contact with the inner side of the support pipe 28. The upper end cap 46 can be connected detachably or undetachably to the adapter ring 54 via a locking connection or cement bond. Above the adapter ring 54, the upper end cap is provided with a short pipe section 56 having slots 58 that extend in the direction of the longitudinal axis 24. The elasticity of the pipe section 56 achieved by the slots 58 allows the filter apparatus 10 to be easily inserted into a suitable receiver (not shown) without tools. A handle 60, for example, in the form of an grip, can be placed around the articulation sites 50 located facing one another to be able to easily handle the filter apparatus 10. The handle 60, when it is not needed, can be fixed on catch projections 62 of the adapter ring 54. For connecting filter element 16 to the adapter ring 54, a cement bond or a detachable connection, for example, in the form of a screw union, can be provided.

The further or second filter element 22 is located in the lower part of the filter apparatus 10, as viewed in FIG. 1, and projects into the filter housing 12. The filter bed 14 comprises the other cylindrical filter element 22 aligned around the longitudinal axis 24. A preferably pleated filter mat 64 of the filter element 22 on the outer side surrounds a support pipe 66 defining a hollow space therein. The filter fineness of the filter mat 64 is chosen such that it is finer than the particle size of the mixture of ion-exchange resins of the filter bed 14.

The longitudinal extension of filter element 22 in the direction of the longitudinal axis 24 corresponds roughly to the longitudinal extension of filter element 16 on the opposite end of the filter apparatus.

Filter element 22 is supported by a base part 68 made with its foot part 70 as an end cap for the filter housing 12. Head part 72 of base part 68 is located in coaxial arrangement to the longitudinal axis 24 of the filter housing 12 and has another passage opening 74 for exit of the fluid cleaned by the filter apparatus 10.

The second filter element 22 on its end opposite a base part 68 is sealed with an end cap 80 having its edge region with a peripheral U-shaped cross-sectional profile open to the bottom. The end cap radially inner leg adjoins the inner wall of the support pipe 66, and radially outer leg adjoins the outer wall of the filter 64 of the second filter element 22. On the end of the second filter element 22 opposite the end cap 80, filter element 22 with its support pipe 66 is put over the head part 72 that projects beyond the base part 68 in the manner of a fitting. The outer side of the filter mat 64 adjoins a peripheral web 78 located on the base part 68 spaced radially from the head part 72. A cement bond connects the end cap 80 and the base part 68 to filter element 22. Detachable connections, for example, in the form of screw unions, can also be implemented.

The flow path 20 of the fluid leads first in the axial flow direction 18 out of the filter bed 14 into the radially outer region of the second filter element 22 and into filter element 22. The fluid then flows in radial flow direction 18 to finally leave filter element 22 and then again in the axial flow direction 18 through the other passage opening 74. The foot part 70 of the base part 68 has another peripheral outer ring 76 with which the foot part 70 is in contact with the outer side 34 of the filter housing 12 and can be connected, for example, by a cement bond. The base part 68, made preferably in one piece, thus terminates the filter apparatus 10, aside from the intended passage opening 74, forming a seal downward.

On the end cap 80 closing the second filter element 22, parts of the filter bed 14 in the form of a column are supported in the manner of a first column, which column, as viewed in FIG. 1, projects above the end cap 80 as far as the level 42 of the filter bed 14. In this connection, the diameter of the first column supported by the end cap 80 is smaller than the diameter of the passage opening 40 of the holding device 30. A further or second column of the filter bed located concentrically to the first column and supported on the base part 68 of the filter housing 12 stabilizes the first column. The first column is supported on the end cap 80 in the axial direction. In the installed state of the filter apparatus 10 shown in FIG. 1, the filter bed 14 above the second filter element 22 forms a closed cylindrical function block whose installation size, viewed in the direction of the longitudinal axis 24 of the filter apparatus, is larger than the correspondingly viewed installation size of the second filter element 22. In particular, the longitudinal extension of the cylindrical function block can correspond to two to ten times the corresponding installation size of the second filter element 22. The indicated columns are not detailed in the FIGURE and result from imaginary extensions above the end cap 80 and the support surface of the base part 68 remaining free.

According to the illustrated approximated flow path 20, in the normal operating state the fluid to be cleaned flows first in radial flow direction 18 through the first filter element 16 to be partially cleaned. At least partially diverted by the sloped surface 48 of the upper cap 46, the fluid on the further flow path 20 in the axial flow direction 18 flows through the filter bed 14 that forms a type of trickle bed. Then, the fluid is diverted into radial flow direction 18 and flows through the second filter element 22 for extremely fine filtration. The fluid cleaned in this way leaves the filter apparatus 10 in the axial flow direction 18.

When installed in a bypass flow of a hydraulic system 100, in order to prevent an accumulation of air in the fluid, the filter apparatus 10 in its operating position shown in FIG. 1 can be located with its filter element 16 below the fluid level 82 of the fluid to be cleaned.

The filter apparatus 10 is suitable not only for removing the indicated contaminants, such as acids, metallic soaps, and basic media, but also, for example, for removing long-chain alcohols.

While one embodiment has been chosen to illustrate the invention, it will be understood by those skilled in the art that various changes and modifications can be made therein without departing from the scope of the invention as defined in the appended claims.

What is claimed is:

1. A filter apparatus for cleaning functional fluid, comprising:
   a filter housing having a longitudinal axis;
   a filter bed inserted in said filter housing having a mixture of anionic and cationic ion-exchange resins;
   a first filter element located upstream of said filter bed and formed as a first flow guide device diverting fluid between a radial flow direction and an axial flow direction relative to said longitudinal axis, said first filter element having a first peripheral filter mat surrounding a hollow space, said first filter element being seated by a holding device on a first axial end of said filter housing, said first filter element having an outer side forming an aligned extension of an outer side of said filter housing; and
   a second filter element located downstream of said filter bed and formed as a second flow guide device diverting fluid between the radial flow direction and the axial flow direction relative to said longitudinal axis, said second filter element having a second peripheral filter mat surrounding a hollow space.

2. A filter apparatus according to claim 1 wherein
   fluid selected from the group consisting of phosphate esters, phosphate-ester based oils, mineral oils and phenols is in said filter housing.

3. A filter apparatus according to claim 1 wherein
   said second filter element is located on a second axial end of said filter housing opposite said first axial end and projects into said filter housing, said filter bed at least partially encompassing said second filter element, said second filter element having a filter fineness that is finer than particle sizes of said mixture.

4. A filter apparatus according to claim 1 wherein
   said holding device is located above said filter bed and comprises a through opening for fluid from which particle dirt has been removed by said first filter element, said through opening being coaxial to said longitudinal axis of said filter housing.

5. A filter apparatus according to claim 4 wherein
   said second filter element is supported by a base part having a foot part being an end cap of said filter housing, having a head part coaxial to said longitudinal axis of said filter housing and having a passage opening for exit of fluid cleared in said first and second filter elements and said filter bed.

6. A filter apparatus according to claim 5 wherein
   said second filter element is sealed on an end thereof opposite said base part with an end cap, part of said filter bed being supported on said end cap on said second filter element in a form of a first column.

7. A filter apparatus according to claim 6 wherein
   said first column has a diameter smaller than a diameter of said through opening of said holding device, a second column of said filter bed being arranged concentrically to said first column and stabilizing said first column.

8. A filter apparatus according to claim 7 wherein
   said first and second columns have active volumes of essentially a same size.

9. A filter apparatus according to claim 1 wherein
   in an installed state, said filter bed is above said second filter element and forms a closed cylindrical function block having an installation size along said longitudinal axis greater than an installation size of said second filter element along said longitudinal axis.

10. A filter apparatus according to claim 1 wherein
in a normal operating state, fluid to be cleaned first flows in a radial direction relative to said longitudinal axis through said first filter element;
fluid partially cleaned in said first filter element flows axially relative to said longitudinal axis through said filter bed forming a trickle bed with said ion-exchange resins;
fluid that has flowed through said filter bed flows in a radial direction relative to said longitudinal axis through said second filter element and is diverted therein for extremely fine filtration; and
fluid that has passed through said second filter element flows from said filter housing axially relative to said longitudinal axis.

11. A filter apparatus according to claim 1 wherein
the filter apparatus is located below a fluid level of a hydraulic system to prevent accumulation of air in fluid in the filter apparatus.

12. A filter apparatus according to claim 1 wherein
said ion-exchange resins are each in granulate form and mixed together to form said filter bed.

13. A filter apparatus according to claim 12 wherein
said filter bed comprises 60% to 95% of anionic ion-exchange resin and 40% to 5% of cationic ion-exchange resin.

14. A filter apparatus according to claim 12 wherein
said filter bed comprises 70% to 90% of anionic ion-exchange resin and 30% to 10% of cationic ion-exchange resin.

15. A filter apparatus according to claim 12 wherein
said filter bed comprises 90% of anionic ion-exchange resin and 10% of cationic ion-exchange resin.

16. A filter apparatus for cleaning functional fluid, comprising:
a filter housing having a longitudinal axis;
a filter bed inserted in said filter housing having a mixture of anionic and cationic ion-exchange resins; and
a first filter element formed as a first flow guide device diverting fluid between a radial flow direction and an axial flow direction relative to said longitudinal axis, said first filter element being seated by a holding device on a first axial end of said filter housing and having an outer side forming an aligned extension of an outer side of said filter housing.

17. A filter apparatus according to claim 16 wherein
fluid selected from the group consisting of phosphate esters, phosphate-ester based oils, mineral oils and phenols is in said filter housing.

18. A filter apparatus according to claim 17 wherein
said holding device is located above said filter bed and comprises a through opening for fluid from which particle dirt has been removed by said first filter element, said through opening being coaxial to said longitudinal axis of said filter housing.

19. A filter apparatus according to claim 18 wherein
said second filter element is supported by a base part having a foot part being an end cap of said filter housing, having a head part coaxial to said longitudinal axis of said filter housing and having a passage opening for exit of fluid cleared in said first and second filter elements and said filter bed.

20. A filter apparatus according to claim 19 wherein
said filter element is sealed on an end thereof opposite said base part with an end cap, part of said filter bed being supported in said end cap on said second filter element in a form of a first column.

21. A filter apparatus according to claim 20 wherein
said first column has a diameter smaller than a diameter of said through opening of said holding device, a second column of said filter bed being arranged concentrically to said first column and stabilizing said first column.

22. A filter apparatus according to claim 21 wherein
said first and second columns have active volumes of essentially a same size.

23. A filter apparatus according to claim 16 wherein
a second filter element formed as a second flow guide device is located on a second axial end of said filter housing opposite said first axial end and projects into said filter housing, said filter bed at least partially encompassing said second filter element, said second filter element having a filter fineness that is finer than particle sizes of said mixture.

24. A filter apparatus according to claim 23 wherein
in an installed state, said filter bed is above said second filter element and forms a closed cylindrical function block having an installation size along said longitudinal axis greater than an installation size of said second filter element along said longitudinal axis.

25. A filter apparatus according to claim 23 wherein
in a normal operating state, fluid to be cleaned first flows in a radial direction relative to said longitudinal axis through said first filter element;
fluid partially cleaned in said first filter element flows axially relative to said longitudinal axis through said filter bed forming a trickle bed with said ion-exchange resins;
fluid that has flowed through said filter bed flows in a radial direction relative to said longitudinal axis through said second filter element and is diverted therein for extremely fine filtration; and
fluid that has passed through said second filter element flows from said filter housing axially relative to said longitudinal axis.

26. A filter apparatus according to claim 16 wherein
the filter apparatus is located below a fluid level of a hydraulic system to prevent accumulation of air in the fluid in the filter apparatus.

27. A filter apparatus according to claim 16 wherein
said ion-exchange resins are each in granulate form and mixed together to form said filter bed.

28. A filter apparatus according to claim 27 wherein
said filter bed comprises 60% to 90% of anionic ion-exchange resin and 40% to 5% of cationic ion-exchange resin.

29. A filter apparatus according to claim 27 wherein
said filter bed comprises 70% to 90% of anionic ion-exchange resin and 30% to 10% of cationic ion-exchange resin.

30. A filter apparatus according to claim 27 wherein
said filter bed comprises 90% of anionic ion-exchange resin and 10% of cationic ion-exchange resin.

31. A filter apparatus according to claim 16 wherein
said holding device is located above said filter bed and comprises a through opening for fluid from which particle dirt has been removed by said first filter element, said through opening being coaxial to said longitudinal axis of said filter housing.

* * * * *